United States Patent
Feng et al.

(10) Patent No.: US 7,794,995 B2
(45) Date of Patent: Sep. 14, 2010

(54) PURIFIED PKB SER 473 KINASE AND USES THEREOF

(75) Inventors: Jianhua Feng, Basel (CH); Brian A Hemmings, Bettingen (CH); Michelle M Hill, Fairfield (AU)

(73) Assignee: Novartis Forschungsstiftung Zweigniederlassung Friedrich Miescher Institute for Biomedical Research, Basel (CH)

( * ) Notice: Subject to any disclaimer, the term of this patent is extended or adjusted under 35 U.S.C. 154(b) by 519 days.

(21) Appl. No.: 10/517,904

(22) PCT Filed: Jun. 12, 2003

(86) PCT No.: PCT/EP03/06193
§ 371 (c)(1), (2), (4) Date: Dec. 10, 2004

(87) PCT Pub. No.: WO03/106669
PCT Pub. Date: Dec. 24, 2003

(65) Prior Publication Data
US 2005/0250167 A1    Nov. 10, 2005

(30) Foreign Application Priority Data
Jun. 13, 2002    (GB) ................ 0213614.1

(51) Int. Cl.
*C12N 9/12* (2006.01)
*C12N 9/10* (2006.01)
*C12N 9/00* (2006.01)
*C12Q 1/00* (2006.01)

(52) U.S. Cl. ........... 435/194; 435/193; 435/183; 435/4

(58) Field of Classification Search ............ 435/194
See application file for complete search history.

(56) References Cited

U.S. PATENT DOCUMENTS

| | | | | |
|---|---|---|---|---|
| 6,001,622 | A * | 12/1999 | Dedhar et al. | 435/194 |
| 6,322,962 | B1 * | 11/2001 | Brown et al. | 435/4 |
| 6,342,495 | B1 * | 1/2002 | Joly et al. | 514/221 |
| 2002/0040275 | A1 * | 4/2002 | Cravatt et al. | 702/19 |

FOREIGN PATENT DOCUMENTS

| WO | WO 97 22360 | 6/1997 |
|---|---|---|
| WO | WO 0036135 | 6/2000 |
| WO | WO 0056864 | 9/2000 |

OTHER PUBLICATIONS

Toker, A. et al., 2000, J. Biol. Chem., 275, 8271-8274.*
Matsuzaki, H., 1996, FEBS Letters, 396, 305-308.*
Alessi, et al., "Characterization of a 3-phosphoinositide-dependent Protein Kinase Which Phosphorylates and Activates Protein Kinase Bα", Current Biol., vol. 7, pp. 261-269 (1997).

(Continued)

*Primary Examiner*—Ruth A Davis
*Assistant Examiner*—Sheridan R Macauley
(74) *Attorney, Agent, or Firm*—Hoxie & Associates LLC

(57) ABSTRACT

This invention provides purified PKB Ser 473 kinase and methods of purifying it. The methods involve the use of several sequential steps, including subcellular fractionation to isolate a plasma membrane fraction and the use of gel filtration or chromatography that separates molecules according to their size or affinity.

6 Claims, 2 Drawing Sheets

OTHER PUBLICATIONS

Alessi, et al., "Mechanism of Activation of Protein Kinase B by Insulin and IGF-1", The Embo J., vol. 15, pp. 6541-6551 (1996).

Andjelkovic, et al., "Role of Translocation in the Activation and Function of Protein Kinase B", J. of Biol. Chem., vol. 272, pp. 31515-31524 (1997).

Andjelkovic, et al., "Activation and Phosphorylation of a Pleckstrin Homology Domain Containing Protein Kinase (RAC-PK/PKB) Promoted by Serum and Protein Phosphatase Inhibitors", Proc. Natl. Acad. Sci., vol. 93, pp. 5699-5704 (1996).

Andjelkovic, et al., "Domain Swapping Used to Investigate the Mechanism of Protein Kinase B Regulation by 3-Phosphoinositide-dependent Protein Kinase 1 and Ser473 Kinase", Mol. and Cell Biol., vol. 19, pp. 5061-5072 (1999) *.

Balendran, et al., "PDK1 Acquires PDK2 Activity in the Presence of a Synthetic Peptide Derived from the Carboxyl Terminus of PRK2", Curr. Biol., vol. 9, pp. 393-404 (1999).

Bickel, et al., "Flotillin and Epidermal Surface Antigen Define a New Family of Caveloe-associated Integral Membrane Proteins", J. Biol. Chem., vol. 272, pp. 13793-13802 (1997).

Brazil, et al., "Ten Years of Protein Kinase B Signalling: A Hard Akt to Follow", Trends in Bio. Sci., vol. 26, pp. 657-664 (2001).

Cantley, et al., "New Insights into Tumor Suppression: PTEN Suppresses Tumor Formation by Restraining the Phosphoinositide 3-Kinase/Akt Pathway", Proc. Natl. Acad. Sci., vol. 96, pp. 4240-4245 (1999).

Coffer, et al., "Protein Kinase B (c-Akt): A Multifunctional Mediator of Phosphatidylinositol 3-Kinase Activation", Biochem. J., vol. 335, pp. 1-13 (1998).

Cote, et al., "Generation of Human Monoclonal Antibodies Reactive with Cellular Antigens", Proc. Natl. Acad. Sci., vol. 80, pp. 2026-2030 (1983).

Delcommenne, et al., "Phosphoinositide-3-OH Kinase-dependent Regulation of Glycogen Synthase Kinase 3 and Protein Kinase B/AKT by the Integrin-linked Kinase", Proc. Natl. Acad. Sci., vol. 95, pp. 11211-11216 (1998).

Downward, "Mechanisms and Consequences of Activation of Protein Kinase B/AKT", Cur. Opin. Cell Biol., vol. 10, pp. 262-267 (1998).

Galbiati, et al, "Emerging Themes in Lipid Rafts and Caveolae", Cell, vol. 106, pp. 403-411 (2001).

Graham, et al., "Characteristics of a Human Cell Line Transformed by DNA from Human Adenovirus Type 5", J. Gen. Virol., vol. 36, pp. 59-74 (1977).

Hannigan, et al., "Regulation of Cell Adhesion and Anchorage-dependent Growth by a New B1-Integrin-Linked Protein Kinase", Nature, vol. 379, pp. 91-96 (1996).

Hanahan, et al., "The Hallmarks of Cancer", Cell, vol. 100, pp. 57-70 (2000).

Hill, et al., "Analysis of Protein Kinase B/Akt", Methods in Enzym., vol. 345, pp. 449-463 (2002).

Hill, et al., "Insulin-stimulated Protein Kinase B Phosphorylation on Ser-473 Is Independent of Its Activity and Occurs through a Staurosporine-insensitive Kinase", J. of Bio. Chem., vol. 276, pp. 25643-25646 (2001) *.

Huse, et al., "Generation of a Large Combinatorial Library of the Immunoglobulin Repertoire in Phage Lambda", Science, vol. 246, pp. 1275-1281 (1989).

Jones, et al., "Molecular Cloning and Identification of a Serine/Threonine Protein Kinase of the Second-messenger Subfamily", Proc. Natl. Acad. Sci., vol. 88, pp. 4171-4175 (1991).

Kandel, et al., "The Regulation and Activities of the Multifunctional Serine/Threonine Kinase Akt/PKB", Exp. Cell Res., vol. 253, pp. 210-229 (1999).

Kohler, "Continuous Cultures of Fused Cells Secreting Antibody of Predefined Specificity", Nature, vol. 256, pp. 495-498 (1975).

Kozbor, et al., "The Production of Monoclonal Antibodies from Human Lymphocytes", Imm. Today, vol. 4, pp. 72-79 (1983).

Lynch, et al., "Integrin-Linked Kinase Regulates Phosphorylation of Serine 473 of Protein Kinase B by an Indiriect Mechanism", Oncogene, vol. 18, pp. 8024-8032 (1999).

Orlandi, et al., "Cloning Immunoglobulin Variable Domains for Expression by the Polymerase Chain Reaction", PNAS, vol. 86, pp. 3833-3837 (1989).

Park, et al., "Identification of Tyrosine Phosphorylation Sites on 3-Phosphoinositide-dependent Protein Kinase-1 and Their Role in Regulating Kinase Activity", J. Bio. Chem., vol. 276, pp. 37459-37471 (2001).

Simons, et al., "Lipid Rafts and Signal Transduction", Nature Rev., vol. 1, pp. 31-40 (2000).

Stephens, et al., "Protein Kinase B Kinases that Mediate Phosphatidylinositol 3, 4, 5-trisphosphate-dependent Activation of Protein Kinase B", Science, vol. 279, pp. 710-714 (1998).

Stillman, et al., "Replication and Supercoiling of Simian Virus 40 DNA in Cell Extracts from Human Cells", Mol. and Cell. Biol., vol. 5, pp. 2051-2060 (1985).

Stokoe, et al., "Dual Role of Phosphatidylinositol-3, 4, 5-trisphosphate in the Activation of Protein Kinase B", Science, vol. 277, pp. 567-570 (1997).

Toker, et al., "Akt/Protein Kinase B Is Regulated by Autophosphorylation at the Hypothetical PDK-2 Site", J. of Biol. Chem., vol. 275, pp. 8271-8274 (2000).

VanHaesebroeck, et al., "The PI3K-PDK1 Connection: More than Just a Road to PKB", Biochem., J., vol. 346, pp. 561-576 (2000).

Vazquez, et al., "The PTEN Tumor Suppressor Protein: An Antagonist of Phosphoinositide 3-Kinase Signaling", Biochimica et Biophysica Acta, vol. 1470, pp. M24-M35 (2000).

Williams, et al., "The Role of 3-Phosphoinositide-dependent Protein Kinase 1 in Activating AGC Kinases Defined in Embryonic Stem Cells", Curr. Biol., vol. 10, pp. 439-448 (2000).

Winter, et al., "Man-made Antibodies", Nature, vol. 349, pp. 293-299 (1991).

Yang, et al., "Molecular Mechanism for the Regulation of Protein Kinase B/Akt by Hydrophobic Motif Phosphorylation", Mol. Cell, vol. 9, pp. 1227-1240 (2002).

Zervas, et al., "Drosophila Integrin-linked Kinase Is Required at Sites of Integrin Adhesion to Link the Cytoskeleton to the Plasma Membrane", J. of Cell Biol., vol. 152, pp. 1007-1018 (2001).

Kroner, et al., "Dual Regulation of . . .", J. Biol. Chem., vol. 275, pp. 27790-27798 (2000).*

Peterson, et al., "Kinase Phosphorylation . . .", Curr. Biol., vol. 9, pp. R521-R524 (1999).*

Hill, et al, "Identification of a Plasma Membrane Raft-associated PKB Ser473 Kinase Activity that Is Distinct from ILK and PDK1", Curr. Biol., vol. 12, pp. 1251-1255 (2002).*

Rane, et al., "P38 Kinase-dependent Mapkapk-2 Activation Functions as 3-phosphoinositide-dependent Kinase-2 for Akt in Human Neutrophils", J. of Biol. Chem., vol. 276, pp. 3517-3523 (2001).*

Balendran, et al, "PKD1 Acquires PDK2 Activity in the Presence of a Synthetic Peptide Derived from the Carboxyl Terminus of PRK2", Curr. Biol., vol. 9, pp. 393-404 (1999).*

Persad, et al., "Regulation of Protein Kinase B/Akt-serine 473 Phosphorylation by Integrin-linked Kinase: Critical Roles for Kinase Activity and Amino Acids Arginine 211 and Serine 343", J. of Biol. Chem., vol. 276, pp. 27462-27469 (2001).*

Brazil, et al., "Ten Years of Protein Kinase B Signalling: A Hard Akt to Follow", TIBS Trends in Bio. Sci., vol. 26, pp. 657-664 (2001).*

Troussard, et al., "Conditional Knock-out of Integrin-linked Kinase Demonstrates an Essential Role in Protein Kinase B/Akt Activation", J. of Biol. Chem., vol. 278, pp. 22374-22378 (2003).*

Tokar; Akt signaling: a damaging interaction makes good; Trends in Biochemical Sciences; 2008; vol. 33, No. 8; pp. 356-359; Department of Pathology, Beth Israel Deaconess Medical Center, Harvard Medical School, Boston, MA.

Anderson, K.E. et al., Translocation of PDK-1 to the plasma membrane is important in allowing PDK-1 to activate protein kinase B, Current Biology, 1998, 8, pp. 684-691.

* cited by examiner

PURIFIED PKB SER 473 KINASE AND USES THEREOF

This application is a U.S. filing under 35 U.S.C. 371 of PCT/EP03/06193, filed on Jun. 12, 2003, which claims the benefit of GB 0213614.1 filed on Jun. 13, 2002, the disclosures of each of which are incorporated herein by reference. The current invention relates to a kinase active in the protein kinase B (PKB) signaling pathway and to the use of the kinase, and to methods of identifying modulators thereof. More particularly, the present invention relates to a purified kinase that phosphorylates the Ser 473 residue of PKB in vivo, and to a method of identifying molecules that regulate signal transduction through the kinase.

BACKGROUND OF THE INVENTION

Reversible protein phosphorylation is a major mechanism for the co-ordinated control of many fundamental cellular functions in eukaryotic organisms, including metabolism, growth, and differentiation. The phosphorylation status, and consequently the activity, of specific target proteins is regulated by the opposing actions of protein kinases and protein phosphatases. Generally, these enzymes are specific either for serine/threonine or for tyrosine phosphoacceptors, although some dual specificity kinases and phosphatases have also been described. The importance of phosphorylation cascades is reflected by the finding that many kinases, phosphatases, and the signal transduction pathways in which they participate have been highly conserved during the course of evolution.

It has become increasingly clear over the last 10 years that the products of most of the genes involved in cellular transformation and cancer i.e. oncogenes and tumour suppressor genes are components of signal transduction pathways (Hanahan and Weinberg, 2000, Cell, 100, 57-70). Protein kinase B (PKB) has been well established as an important signalling intermediate, and its de-regulation has been implicated in the development of human cancer and diabetes (reviewed in Brazil and Hemmings, (2001), Trends Biochem Sci 26: 657-64).

Protein kinase B (c-Akt/PKB) is an ubiquitous Ser/Thr protein kinase which has a complex mechanism of regulation yet to be completely resolved (Downward et al., 1998, Curr. Opin. Cell Biol., 10, 262-267; Coffer et al., 1998, Biochem. J., 335, 1-13; Kandel and Hay, 1999, Exp. Cell Res., 253, 210-229; Vanhaesebroeck and Alessi, 2000, Biochem. J. 346 Pt 3, 561-576). Upon cell stimulation, localized generation of phosphatidylinositol 3,4,5-trisphosphate ($PIP_3$) at the plasma membrane recruits PKB to the membrane through its N-terminal pleckstrin homology (PH) domain. PKB is then activated by phosphorylation on two regulatory sites: Thr308 in the activation loop in the kinase domain and Ser473 in the hydrophobic C-terminal regulatory domain (Alessi et al., 1996, EMBO J., 15, 6541-6551).

In cells lacking the tumour suppressor PTEN (a lipid phosphatase), PKB is more active (Cantley and Neel, 1999, Proc. Natl. Acad. Sci. USA, 96, 4240-4245; Vazquez and Sellers, 2000, Biochim. Biophys. Acta, 1470, M21-M35), as a result of the increase in phosphorylation at Thr 308 and Ser 473. The kinase PDK1, a kinase that contains a PH domain, has been shown to be able to phosphorylate PKB at Thr-308 in vivo (Alessi et al., 1997, Curr. Biol., 7, 261-269; Stokoe et al., 1997, Science, 277, 567-570; Stephens et al., 1998, Science, 279, 710-714). Despite PDK1 being identified as the PKB Thr308 kinase, the kinase responsible for phosphorylating Ser473 in vivo, often referred to as PDK2 or Ser473 kinase, remains elusive.

Several kinases have been reported to possess Ser473 phosphorylating activity, including mitogen-activated protein kinase-activated kinase-2 (MAPKAPK-2) (Alessi et al., 1996, EMBO J., 15, 6541-6551), integrin-linked kinase (Delcommenne et al., (1998), Proc Natl Acad Sci USA 95: 11211-11216), PDK1 (Balendran et al., (1999), Curr Biol 9: 393-404; WO 00/36135) and PKB (Toker and Newton, (2000), J Biol Chem 275: 8271-8274). However, evidence has been presented which argues against these kinases as the physiological PKB Ser473 kinase. For example, activation of MAPKAPK-2 is PI3-kinase-independent, whereas PKB Ser473 phosphorylation is sensitive to PI 3-kinase inhibitors (Alessi et al., 1996, EMBO J., 15, 6541-6551). PDK1-null cells undergo Ser473 phosphorylation, suggesting that PDK1 is not required for Ser473 phosphorylation (Williams et al., (2000), Curr Biol 10: 439-448). Furthermore, insulin-stimulated PKB Ser473 phosphorylation does not require activation of PDK1 or PKB, as Ser473 phosphorylation is not sensitive to staurosporine treatment, which inhibits PDK1 and therefore PKB activity (Hill et al., (2001), J Biol Chem 276: 25643-25646).

Another kinase, ILK, was shown to phosphorylate glycogen synthase kinase-3, as well as Ser473 of PKB (Delcommenne et al., (1998), Proc Natl Acad Sci USA 95: 11211-11216). However, it has also been suggested that ILK influences PKB phosphorylation indirectly, as overexpression of certain kinase domain mutants can mimic wild type ILK in inducing Ser473 phosphorylation (Lynch et al., (1999), Oncogene 18: 8024-8032). Moreover, a physiological role of ILK in regulating PKB phosphorylation has been questioned since ILK knockout in *Drosophila melangaster* shows a phenotype more similar to the integrin knockout than to the PKB knockout (Zervas et al., (2001), J Cell Biol 152: 1007-1018).

Developing methods to regulate PKB Ser473 kinase activity requires sources of purified PKB Ser473 kinase. Purified PKB Ser473 kinase would, for example, be useful in developing and testing assays for measuring PKB Ser473 kinase activity, to evaluate the assay and for use as a standard in the assay. Assays for PKB Ser473 kinase are useful in screening for modulators of PKB signaling or other signaling pathways dependent on PKB Ser 473 kinase activity. Purified PKB Ser473 kinase would be more useful than crude cells to identify and test modulators, inhibitors or activators of PKB Ser473 kinase activity in in vitro assays. Such modulators of PKB Ser473 kinase activity would be useful in the treatment of a condition associated with PKB signaling pathways, for example, an anomaly in cell growth or with an anomaly in insulin regulation, such as cancer, diabetes or other PKB-dependent conditions, such as neurodegenerative conditions or erectile dysfunction.

Moreover, purified PKB Ser473 kinase would facilitate a thorough biochemical analysis of the kinase's mechanism, which may provide insight for development of mechanism-based regulators. Purified PKB Ser473 kinase also would be useful in the preparation of antibodies against PKB Ser473 kinase, including phospho-specific antibodies. Such antibodies would in turn be especially useful as reagents to purify human PKB Ser473 kinase and may be useful in cancer diagnosis or prognosis. Purified PKB Ser473 kinase also will help provide amino acid sequence information useful in designing various mutants or fragments of the PKB Ser 473 kinase.

While there is a need for characterization and purification of PKB Ser473 kinase, the purification of the human enzyme has posed technical challenges. Human cells possess high levels of other kinases that might have chromatographic purification properties similar to the PKB Ser473 kinase making purification of PKB Ser473 kinase from human cells particularly difficult. In addition, a specific assay had to be developed to follow the PKB Ser473 kinase activity responsible for PKB phosphorylation in vivo. Thus, there is a need for purified PKB Ser473 kinase and purified human PKB Ser473 kinase, in particular.

SUMMARY OF THE INVENTION

Human PKB Ser473 kinase has been purified to over 5,000-fold purity from cell culture. Two phosphoproteins of 48 kDa and 58 kDa respectively that co-purify with fractions containing PKB Ser473 kinase activity are present in the purified fractions and have been isolated.

In one aspect, the invention provides methods of purifying PKB Ser473 kinase. The steps included in the method depend on the level of purification one desires. A method to purify PKB Ser473 kinase from an impure composition containing organic biomolecules, for example, to at least 5,000-fold compared to crude 293 cell extract involves:
(1) preparing a cell extract from a suitable source of PKB Ser473 kinase, e.g., HEK 293 cells;
(2) isolating plasma membranes by subcellular fractionation; and
(3) treating the plasma membrane fraction with a buffer comprising a detergent, preferably a non-ionic detergent, such as TRITON X-100 and/or a buffer of high ionic strength, e.g., comprising 0.5M NaCl.

Further purification of the resulting PKB Ser 473 kinase preparation can be achieved by using one or more of the following steps: flotation gradient analysis, for example by resuspending TRITON X-100 insoluble proteins and subjecting to sucrose flotation gradient analysis; separating the PKB Ser473 kinase from other organic biomolecules according to molecular size, shape, or buoyant density, for example separating molecules according to size gel filtration on Superdex 200 HR 10/30 and collecting the PKB Ser473 kinase; or separating molecules based on charge (ion exchange chromatography), hydrophobicity or affinity (or lack of affinity) for a particular ligand (e.g., ATP, antibody, staurosporin and peptides).

PKB Ser473 kinase can be purified to substantial purity (e.g., at least 100,000-fold) by further isolating it by gel electrophoresis. PKB Ser473 kinase can be isolated to different levels of purity by altering, changing the sequence of, or eliminating any of the steps in the purification protocol. Other purification steps well known in the art can be added to further improve purification, including without limitation ATP-Agarose affinity chromatography.

The invention also provides a composition comprising PKB Ser473 kinase having at least 2000-fold, preferably at least 3000-, 5000-, 10,000- or 20,000-fold, most preferably at least 50,000- or 100,000-fold increased relative purity compared to crude cell extracts of human embryonic kidney (HEK) 293 cells, which when associated with cellular proteins has a kinase activity and has a molecular weight of 40-1,000 kDa.

The invention also provides purified PKB Ser473 kinase and, more particularly, PKB Ser473 kinase having at least 2000-fold, preferably at least 3000-, 5000-, 10,000- or 20,000-fold, most preferably at least 50,000- or 100,000-fold increased relative purity compared to crude cell extracts of human embryonic kidney (HEK) 293 cells. The PKB Ser473 kinase can be obtained from an animal, in particular a mammal, preferably from a human source. The invention also provides PKB Ser473 kinase made by the purification steps above.

The invention further comprises a purified cell extract that has measurable PKB Ser 473 kinase activity in 0.2 µg of total protein when quantified in a kinase assay, for example, in which a peptide substrate comprising the Ser 473 site of PKB is phosphorylated with labelled phosphate and labelled substrate is detected. Preferably, the kinase elutes with an apparent molecular weight of 40-1,000 kDa, most preferably about 550 kDa when fractionated by gel filtration chromatography, and the kinase is enriched between 3,000-fold and 50,000-fold or more compared with a crude extract of HEK 293 cells.

In another aspect this invention provides methods of inducing an immune response against PKB Ser473 kinase comprising inoculating an animal with purified PKB Ser473 kinase or with an immunogenic fragment thereof, such as a protein component. This includes induction of a humoral immune response that leads to the production of antibodies, as well as a cell-mediated immune response.

In another aspect this invention also provides a polypeptide fragment of a protein component of human PKB Ser473 kinase which, when presented to an animal as an immunogen, elicits a humoral or cell-mediated immune response.

In another aspect, this invention provides a composition comprising an antibody or antibody fragment that specifically binds to a protein component of human PKB Ser473 kinase.

In another aspect, the invention provides a method of screening for a potential modulator of PKB Ser 473 kinase activity comprising the steps of (a) incubating a purified PKB Ser 473 kinase protein as hereinabove described with a compound; determining PKB Ser 473 kinase activity; detecting an alteration in the PKB Ser 473 kinase activity in the presence of the compound relative to when the compound is absent, the alteration being indicative of a potential modulator of PKB Ser 473 kinase activity. A decrease in the PKB Ser 473 kinase activity correlates with the presence of a PKB Ser473 kinase inhibitor, which can be used as an anti-proliferative or anti-tumour compound. An increase in the PKB Ser 473 kinase activity correlates with the presence of a PKB Ser473 kinase activator potentially useful in the treatment of any one or more of a disease or condition requiring increased PKB Ser 473 kinase activity including without limitation diabetes, neurodegenerative conditions, and erectile dysfunction.

Therefore, the invention also provides a method of screening for potential modulators of tumour cell growth, in particular inhibitors of tumour cell growth, as well as modulators of PKB Ser 473 kinase activity.

In one aspect of the present invention, a compound identified by the screening method can be used as a pharmaceutical. In another aspect, the compound identified by the screening method can be used for the manufacture of a medicament for the treatment or prophylactic treatment of a disease or condition associated with cell growth. The compound identified by the screening method can further be used in the treatment of a condition associated with cell growth, especially for inhibiting cancer cell growth. A method for inhibiting cancer cell growth comprises contacting a cancerous cell with a PKB Ser 473 kinase inhibitor.

In another aspect of the present invention, the compounds identified by the screening method are used for treating a disease associated with an anomaly in cell growth comprising administering to a subject a pharmaceutically effective amount of a PKB Ser 473 kinase inhibitor. In an alternative embodiment, compounds are provided for treating a disease associated with an anomaly in insulin regulation.

DRAWINGS

DETAILED DESCRIPTION OF THE INVENTION

Figure 1:
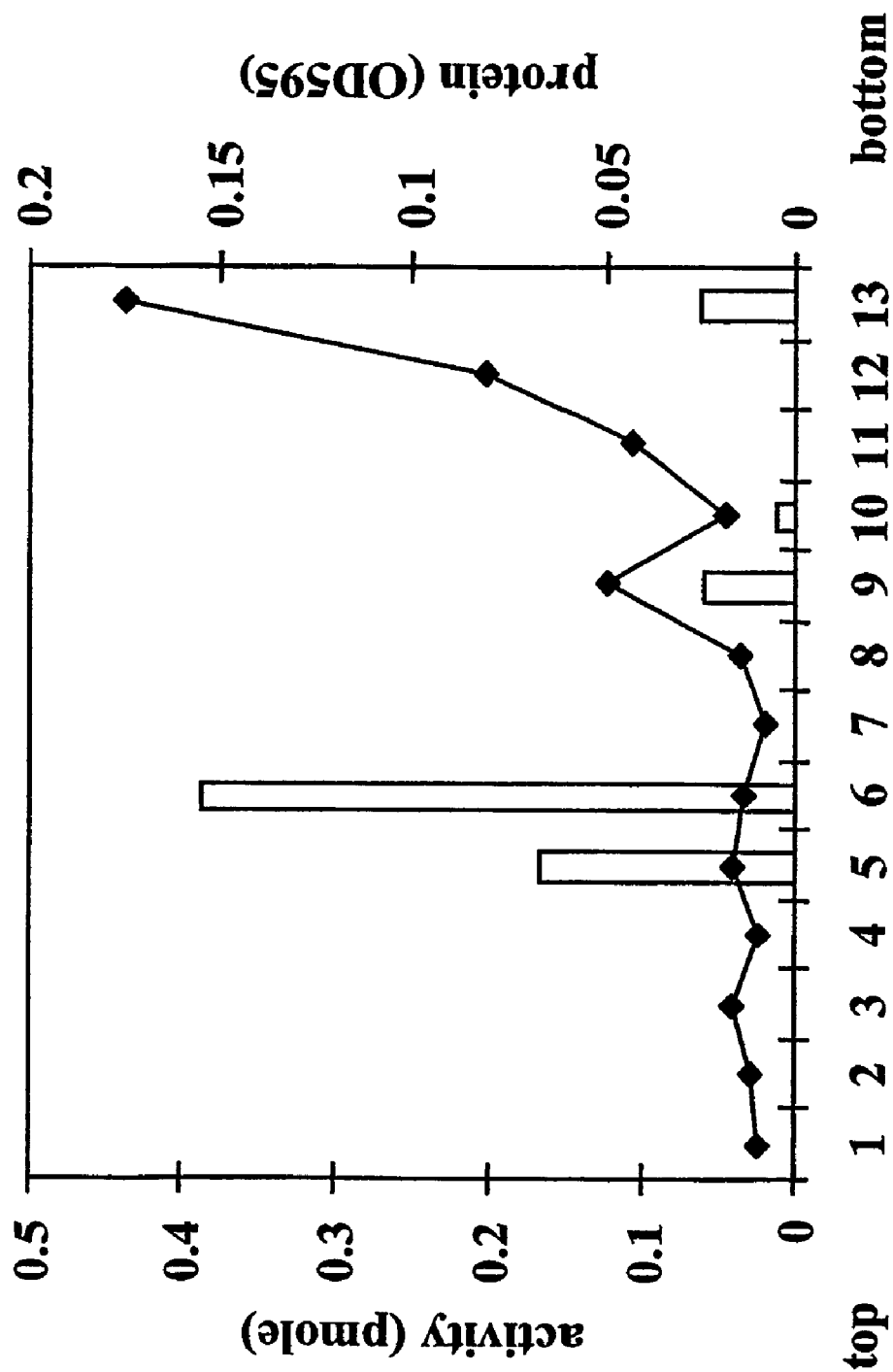
FIG. 1 is a schematic diagram of Ser473 kinase activity (bars) in 5-40% sucrose flotation gradients.

Full activation of protein kinase B (PKB/Akt) requires phosphorylation on residues Thr308 and Ser473. To date, the identity of the Ser473 kinase has remained unclear. The present inventors have isolated, purified and characterized a constitutively active PKB Ser473 kinase activity enriched in buoyant, detergent-insoluble plasma membrane rafts, distinct from the cytosolic distribution of PKB and 3-phosphoinositide-dependent kinase-1 (PDK-1). This Ser473 kinase activity is released from the membrane by high salt, and gel filtration analysis shows that the kinase responsible is present In a large complex of about 500 kDa. Two major phosphoproteins of 48 kDa and 58 kDa were detected in partially purified PKB Ser473 kinase preparations. In contrast to previous observations, the present inventors could show that integrin-linked kinase (ILK) immunoprecipitates do not retain Ser473 kinase activity. Thus, the inventors have identified a raft-associated PKB Ser473 kinase that plays a role in PKB signalling and is different from ILK.

The invention provides purified PKB Ser473 kinase and methods of making it. In particular, this invention is directed to purified mammalian or human PKB Ser473 kinase and recombinant PKB Ser473 kinase. This invention provides purified PKB Ser473 kinase isolated from any cells expressing PKB Ser 473 kinase, for example, crude extracts of normal cells, cancer cells, immortalized cells, human or animal tissues, tumours, or from cells expressing PKB Ser 473 kinase recombinantly.

In one embodiment of the present invention, human PKB Ser473 kinase is purified to over 50,000-fold purity over crude cell extract from HEK 293 cells. Two phosphoproteins of 48 kDa and 58 kDa respectively that co-purify with fractions containing PKB Ser473 kinase activity are present in the purified fractions and have been isolated.

The invention provides a composition comprising PKB Ser473 kinase having at least 2000-fold, at least 3000-fold, at least 5000-fold, at least 10,000-fold, at least 20,000-fold, at least 50,000-fold, or at least 100,000-fold increased relative purity compared to crude cell extracts of 293 cells, which when associated with cellular proteins has a Ser 473 kinase activity and has an apparent molecular weight of about 550 kDa upon gel filtration on Superdex 200. As is apparent to one of ordinary skill in the art, variation in the apparent molecular weight will be found dependent on the chromatographic conditions and the matrix used. Typically, the Ser 473 kinase would be expected to elute corresponding to a size of between 450 and 650 kDa, more particularly corresponding to a size between 500 and 600 kDa.

"Purified PKB Ser473 kinase" refers to PKB Ser473 kinase preparations having at least 2000-fold increased relative purity over crude HEK 293 cell extracts. As used herein, a PKB Ser473 kinase preparation has 2000-fold increased relative purity if the specific activity of PKB Ser473 kinase in the preparation is at least 2000 times greater than the specific activity of PKB Ser473 kinase of crude whole cell extracts of suspension-capable 293 cells, described herein below, and as measured by an in vitro kinase assay, such as that described herein below in Example 1. "Substantially pure" means an object species is the predominant species present (i.e., on a molar basis, more abundant than any other individual organic biomolecular species in the composition), and a substantially purified fraction is a composition wherein the object species comprises at least about 50% (on a molar basis) of all organic biomolecular species present. Generally, a substantially pure composition means that about 80% to 90% or more of the organic biomolecular species present in the composition is the purified species of interest. The object species is purified to essential homogeneity (contaminant species cannot be detected in the composition by conventional detection methods) if the composition consists essentially of a single organic biomolecular species. "Organic biomolecule" refers to an organic molecule of biological origin, e.g., proteins, nucleic acids, carbohydrates or lipids. Solvent species, small molecules (<500 Daltons), stabilizers (e.g., BSA), and elemental ion species are not considered organic biomolecular species for purposes of this definition.

"PKB Ser473 kinase" or "Ser 473 kinase" are used interchangeably herein and refer to the kinase that is responsible for phosphorylation of the Ser473 site of PKB in vivo. Although reference is made herein to Ser473, it will be apparent to one of ordinary skill in the art that the numbering of this site may change dependent on which kinase or kinase isoform is phosphorylated. Thus, the regulatory phosphorylation site, which typically lies within the hydrophobic motif, is Ser-473 of PKBα, Ser-474 of PKBβ and Ser 472 of PKBγ for PKB. The PKB Ser473 kinase is thought not only to be responsible for phosphorylation of these PKB isomers in vivo at these sites, but also for the corresponding sites of other kinases of similar structure. The regulatory phosphorylation site of these kinases is found in the regulatory segment that contains a hydrophobic motif of at least four amino acids and typically six amino acid residues in length, which typically contains the sequence FXXF, e.g. FXXFXY/F or FXXF(S/T)(Y/F), although the kinase NDR has the sequence FXXY at this position, where X represents any amino acid. The regulatory phosphorylation site typically lies within the hydrophobic motif, for example, PKBalpha, beta and gamma all have the sequence FPQFSY within their regulatory segment. In particular, other kinases will include AGC family members, including without limitation SGK, p70S6K, p90RSK, PKC, NDR, or any kinase with a hydrophobic motif, which can be phosphorylated by the Ser473 kinase of the present invention.

In methods of purifying PKB Ser473 kinase it is often useful to determine the presence or amount of PKB Ser473 kinase or PKB Ser473 kinase activity in a preparation. The present inventors have developed a specific assay to identify the Ser 473 kinase and the Ser 473 kinase activity. In this assay, as described in Example 1, Ser473 kinase activity In subcellular fractions generated from HEK 293 cells is measured in vitro using two peptides as substrates: RRPHFPQF SYSASSTA (FSY peptide; SEQ ID NO:1), corresponding to the last 16 amino acids of PKBα, and a control peptide, RRPHFPQFAYSASSTA (SEQ ID NO:2), where Ser473 is changed to an alanine (FAY peptide). These two peptides are used as substrates for several reasons. By using the FSY and FAY peptides it is possible to conveniently identify a kinase activity specific for the Ser473 site. Results with the FAY peptide indicate the existence of kinase activity In the partially purified fractions capable of phosphorylating other Ser/Thr or Tyr residues in this sequence. Therefore, by monitoring kinase activity using both peptides as substrates, specific Ser473 kinase activity can be detected. Typically, protein concentration will also be determined at each stage of purification using methods known in the art (e.g., Bradford colorimetric method).

This invention further provides methods of making purified PKB Ser473 kinase from an impure composition, i.e., a composition containing PKB Ser473 kinase and other contaminating organic biomolecules. The steps included in the method depend on the level of purification one desires. A method of purifying PKB Ser473 kinase from an impure composition containing other organic biomolecules, for example from a crude cell extract of HEK 293 cells, to at least 5,000-fold compared to crude extract involves:
(1) preparing a cell extract from a suitable source of PKB Ser473 kinase, e.g., HEK 293 cells;
(2) isolating plasma membranes by subcellular fractionation; and
(3) treating the plasma membrane fraction with a buffer comprising a detergent, preferably a non-ionic detergent, such as TRITON X-100 and/or a buffer of high ionic strength, e.g., comprising 0.5M NaCl.

Further purification of the resulting PKB Ser 473 kinase preparation can be achieved by using one or more of the following steps: flotation gradient analysis, for example by resuspending TRITON X-100 insoluble proteins and subjecting to sucrose flotation gradient analysis; separating the PKB Ser473 kinase from other organic biomolecules according to molecular size, shape, or buoyant density, for example separating molecules according to size gel filtration on Superdex 200 HR 10/30 and collecting the PKB Ser473 kinase; or separating molecules based on charge (ion exchange chromatography), hydrophobicity or affinity (or lack of affinity) for a particular ligand (e.g., ATP, antibody, staurosporin and peptides). Thus, PKB Ser473 kinase can be isolated to different levels of purity by altering, changing the sequence of, or eliminating any of the steps in the purification protocol.

PKB Ser473 kinase can be isolated to at least 50,000-fold purity by adding an affinity step, for example, using staurosporine-affinity chromatography to separate the sensitive and insensitive kinase activities. Thus, PKB Ser 473 kinase may be further purified by its inability to bind to a specific matrix, whereby similar, contaminating bioorganic molecules are removed through binding to the matrix. Other affinity purification steps well known in the art can be added to further improve purification, including without limitation ATP-Agarose affinity chromatography or affinity matrices made with antibodies specific for PKB Ser 473 kinase. Thus, PKB Ser 473 kinase will bind to specific affinity matrices and contaminating materials removed prior to elution of the PKB Ser473 kinase. PKB Ser473 kinase can be purified to substantial purity (e.g., at least 100,000-fold) by further isolating it by gel electrophoresis.

The specific purification steps used and their sequence is at the discretion of the practitioner. However, the following guidance is provided. In general, it is preferred to begin with steps having high capacity and relatively low selectivity, followed by steps having intermediate capacity and/or selectivity, followed by steps having low capacity and high selectivity. It is preferred to use plasma membrane fractions and not cytosol or nuclear fractions of cells, as substantial purification is achieved through the cellular fractionation.

Purification steps having intermediate selectivity and capacity are preferred after high capacity steps. These include matrices of intermediate selectivity and separation based on molecular size, shape or buoyant density. While purification with intermediate selectivity resins is preferred first, the intermediate purification steps need not be limited to any particular order or number.

Specific affinity matrices have relatively low capacity, but high selectivity, and are preferred later in the purification process when PKB Ser473 kinase is present with fewer contaminating materials. This step can be a sole purification step and is most useful when PKB Ser473 kinase has at least 40-fold increased relative purity.

Purification of PKB Ser473 kinase begins with an impure source composition, such as a crude cell extract, preferably rich in PKB Ser473 kinase activity. Cell lines are a particularly useful source of crude PKB Ser473 kinase preparations because they can be cultured and harvested in large quantities, thereby providing cellular fractions for large-scale PKB Ser473 kinase preparations. In particular, in the preparation of purified human PKB Ser473 kinase, 293 cells are preferred. 293 cells are of human embryonic kidney origin that have been transformed with fragments of adenovirus type 5 DNA (Graham et al., 1977 J. Gen. Virol. 36:59-77). The cell line, which grows in monolayer cultures, was adapted to growth in suspension by Stillman and Gluzman, (1985) Mol. and Cell Bio. 5:2051-2060). They are available from the American Type Culture Collection (ATCC) (Accession No. ATCC CRL 1573).

Other cell types, particularly those that grow readily in suspension cultures (which facilitates large scale culturing), also are useful for purifying human PKB Ser473 kinase. Candidates include cell lines of B or T cell lineage, such as Namalwa (Burkitt's lymphoma), Daudi (Burkitt's lymphoma), Jurkat (acute T cell leukemia) and HUT 78 (cutaneous T cell lymphoma) lines. HeLa cells (cervical carcinoma) can also be used as a source of PKB Ser473 kinase activity. Nevertheless, tissues may also be used as a source of PKB Ser 473 kinase, such as placenta.

The amount of impure preparation needed to purify PKB Ser473 kinase depends, in part, upon the abundance of PKB Ser473 kinase in the cell, the amount of PKB Ser473 kinase lost at each step, and the ultimate degree of purification and amount desired.

As purification advances, PKB Ser473 kinase becomes both purer and more dilute. In this state, PKB Ser473 kinase can be lost due to PKB Ser473 kinase sticking to tubes, tubing, tips, etc. This loss can be minimized by the addition of detergent, such as 0.1% Nonidet P-40, 1% Tween-20 or other, preferably non-ionic detergents.

The crude cell extract from mammalian cells used in the methods of this invention can be whole cell extract although enrichment of subcellular fractions enriched in the plasma membrane is a preferred initial step in the purification of PKB Ser473 kinase. In order to characterize and purify the PKB Ser473 kinase, the present inventors developed a subcellular fractionation protocol (see Example 1) to generate fractions enriched for plasma membrane. To determine the efficacy of this procedure, the fractionation behavior of two PKB constructs was examined. However, now that the protocol has been established, the distribution of PKB after subcellular fractionation need not be followed unless a control is desired. Clearly, other control markers could be used effectively instead of PKB.

The present invention also provides a way to determine the nature of the association of the Ser473 kinase with the plasma membrane. Extraction of the plasma membrane fraction with a high ionic strength buffer (0.5 M NaCl) releases the Ser473 kinase from the lipid bilayer, with activity detected mainly in the supernatant which shows that the Ser473 kinase is not an integral membrane protein, but is rather associated with the plasma membrane via protein/protein or electrostatic interactions.

Another optional step of the purification protocol of the present invention comprises treating plasma membrane fraction with a detergent, preferably a non-ionic detergent; such as Triton X-100 or a buffer of high ionic strength (e.g. buffer with 0.5M NaCl; see Example 1). When the plasma membrane fraction is treated with 1% Triton X-100, Ser473 kinase activity is highly enriched in the insoluble fraction, whereas high ionic strength buffer releases the Ser473 kinase from the lipid bilayer, with activity mainly in the supernatant (after centrifugation). Alternatively, these steps may be combined sequentially.

In another step of the purification protocol of the present invention comprises sucrose flotation gradients of plasma membrane fractions, for example as described in Example 2 after resuspending of the detergent-insoluble proteins described above. Additional or alternative purification steps may involve gradient centrifugation of the PKB Ser473 kinase in gradients of different compositions that yield separation of the molecules in the preparation, such as glycerol.

Another intermediate purification step in a method to purify PKB Ser473 kinase involves separating the PKB Ser473 kinase from other organic biomolecules according to molecular size, shape, or buoyant density and collecting the PKB Ser473 kinase. This is preferably a step carried out with PKB Ser 473 kinase released from the plasma membrane by high ionic strength buffer and Involves fractionating the PKB Ser473 kinase preparation by gel filtration chromatography. Sizing gel matrices that separate proteins in the size range of 40 kD to 1000 kD are most useful in human PKB Ser473 kinase purification. In particular, the Superdex 200 HR 10/30 column attached to an FPLC system has been demonstrated to be very effective (see Example 3). Other suitable matrices are well known in the art and include HW65 (TosoHaas, Montgomeryville, Pa.), Superose® 6 (Pharmacia, Uppsala, Sweden) and, TSK-Gel*G5000PW.sub.XL.

In a further aspect of the invention, the purification procedure may optionally involve the use of gel electrophoresis, which separates molecules based on their charge, size and shape. The gel compositions may vary widely in this embodiment. A preferred gel is a native gel, composed of agarose, polyacrylamide, or both, that is run under physiological conditions of buffer strength and pH, which tend to preserve the native complex and activity of human PKB Ser473 kinase. Alternatively, SDS-gel electrophoresis may be desired where retaining kinase activity is less important (for example, for sequencing), although some proteins can be easily renatured after SDS-PAGE.

Preferably after the high capacity and intermediate purification steps, PKB Ser473 kinase can be further purified by contacting the PKB Ser473 kinase with an affinity agent having specific affinity for PKB Ser473 kinase, separating PKB Ser473 kinase from other organic biomolecules that do not bind to the affinity agent, and collecting PKB Ser473 kinase from the affinity agent. Affinity agents in this step of the purification method are orders of magnitude more specific for binding PKB Ser473 kinase over other organic biomolecules, than are the agents in the other steps of the method. Affinity agents having specific affinity for PKB Ser473 kinase include, for example, antibodies that recognize epitopes of PKB Ser473 kinase or PKB Ser473 kinase associated proteins, and compounds that inhibit PKB Ser473 kinase or are substrates thereof (e.g., peptides, ATP). Preferably, the affinity agent is attached to a matrix. Then, molecules that have not bound to the affinity agent are separated or removed from the mixture. By releasing PKB Ser473 kinase from the affinity agent, PKB Ser473 kinase is purified. Alternatively, an affinity agent for a suspected contaminant can be used allowing PKB Ser 473, which does not bind to the chosen affinity agent, to be separated from the contaminant, which binds to the matrix. Thus, the affinity agent can be an antibody specific for a contaminant. Typically, the affinity bound bioorganic molecule can be eluted using the affinity agent or high salt, for example.

PKB Ser473 kinase can be further isolated by using saturosporine-affinity chromatography to further separate staurosporine-sensitive and insensitive kinase activities.

After purifying PKB Ser473 kinase to the desired degree of purity, the proteins in fractions containing PKB Ser473 kinase activity can be examined by gel electrophoresis. Two phosphopolypeptides were identified in the purified fractions that co-purified with PKB Ser473 kinase activity. One protein had an apparent molecular mass of 48 kD on SDS-PAGE. Another protein had an apparent molecular mass of 58 kD on SDS-PAGE.

The invention thus provides purified PKB Ser473 kinase having at least 2000-fold, at least 3000-fold, at least 5000-fold, at least 10,000-fold, at least 20,000-fold, at least 50,000-fold, or at least 100,000-fold increased relative purity compared to crude cell extracts of 293 cells. The PKB Ser473 kinase can be animal, mammalian and, more particularly, human. The invention also provides PKB Ser473 kinase made by the purification steps above.

The invention further comprises a purified cell extract that has measurable PKB Ser 473 kinase activity in 0.2 μg of total protein when quantified in a kinase assay, for example, in which a peptide substrate comprising the Ser 473 site of PKB is phosphorylated with labelled phosphate (typically radioactively labelled phosphate) and labelled substrate is detected. Preferably, the kinase elutes with an apparent molecular weight of 40-1,000 kDa, most preferably about 550 kDa when fractionated by gel filtration chromatography, and the kinase is enriched between 3,000-fold and 50,000-fold or more compared with a crude extract of HEK 293 cells.

In another aspect this invention provides methods of inducing an immune response against PKB Ser473 kinase comprising inoculating an animal with purified PKB Ser473 kinase or with an immunogenic fragment thereof. This includes induction of a humoral immune response that leads to the production of antibodies, as well as a cell-mediated immune response.

In another aspect this invention also provides a polypeptide fragment of a protein component of human PKB Ser473 kinase which, when presented to an animal as an immunogen, elicits a humoral or cell-mediated immune response.

In another aspect, this invention provides a composition comprising an antibody or antibody fragment that specifically binds to a protein component of human PKB Ser473 kinase.

"Antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well-characterized fragments produced by digestion with various peptidases. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al (1989) Science 256:1275. The term "antibody," as used herein, also includes antibody fragments either produced by the modification of whole antibodies or those synthesized de novo using recombinant DNA methodologies.

Monoclonal antibodies may be prepared using any technique that provides for the production of antibody molecules by continuous cell lines in culture. These Include but are not limited to the hybridoma technique originally described by Koehler and Milstein (Koehler and Milstein (1975) Nature 256: 495-497), the human B-cell hybridoma technique (Kosbor et al (1983) Immunol Today 4: 72; Cote et al (1983) Proc Natl Acad Sci 80: 2026-2030) and the EBV-hybridoma technique (Cole et al (1985) Monoclonal Antibodies and Cancer Therapy, Alan R Liss Inc, New York N.Y., pp 77-96). Large amounts of monoclonal antibodies for use in immunoassays may be obtained by various techniques familiar to those skilled in the art. Briefly, spleen cells from an animal immunised with the desired protein are immortalised, commonly by fusion with a myeloma cell. Alternative methods of immortalisation include transformation with Epstein Barr Virus, oncogenes, or retroviruses, or other methods well known in the art. Colonies arising from single immortalised cells are screened for production of antibodies of the desired specificity and affinity for fibronectin molecule, variant or fragment thereof, tenascin or syndecan. The yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from appropriate human B cells, i.e. immunised according to a general protocol.

For the production of antibodies, various hosts including goats, rabbits, rats and mice may be immunised by injection with a PKB Ser473 kinase preparation, variant or fragment thereof, or any portion or fragment that retains immunogenic properties. Depending on the host species, various adjuvants may be used to increase immunological response. Such adjuvants are commercially available, and Include but are not limited to Freund's, mineral gels such as aluminium hydroxide, and surface active substances such as lysolecithin, pluronic polyols, polyanions, peptides, oil emulsions, keyhole limpet hemocyanin, and dinitrophenol. BCG (*Bacillus* Calmette-Guerin) and *Corynebacterium parvum* are potentially useful adjuvants.

Animals (e.g. inbred strain of mice or rabbits) can be immunised with Immunogen using a standard adjuvant, such as Freund's adjuvant, and a standard immunisation protocol. Alternatively, a synthetic peptide conjugated to a carrier protein can be used as an immunogen. Polyclonal sera are collected and titered against the immunogen In an immunoassay, for example, a solid phase immunoassay with the immunogen immobilised on a solid support. Polyclonal antisera with a titer of, for example, $10^4$ or greater are selected and tested for their cross-reactivity against homologous proteins from other organisms and/or non-immunogen protein, using, for example, a competitive binding immunoassay. Specific monoclonal and polyclonal antibodies and antisera will usually bind with a $K_D$ of at least about 1 µM, preferably at least about 0.1 µM or better, and most preferably, 0.01 µM or better.

Antibodies may also be produced by inducing in vivo production in the lymphocyte population or by screening recombinant immunoglobulin libraries or panels of highly specific binding reagents (Orlandi et al (1989) Proc Natl Acad Sci 86: 3833; and Winter and Milstein (1991) Nature 349: 293.

An antibody "specifically binds to" or "is specifically immunoreactive with" a protein when the antibody functions in a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. Antibodies may be labeled with useful labels that can include $^{32}P$, $^{35}S$, $^{3}H$, $^{14}C$, $^{126}I$, $^{131}I$, fluorescent dyes (e.g. FITC, rhodamine and lanthanide phosphors), electron-dense reagents, enzymes, e.g. as commonly used in ELISA (e.g. horseradish peroxidase, beta-galactosidase, luciferase and alkaline phosphatase), biotin, dioxigenin, or haptens and proteins for which antisera or monoclonal antibodies are available.

"Immunoassay" refers to an assay that utilizes an antibody to specifically bind an analyte. The immunoassay is characterized by the use of specific binding properties of a particular antibody to isolate, target, and/or quantify the analyte.

Kinases such as PKB are known to be involved in signal transduction within cells. This involvement makes kinases targets for agents that seek to obtain a biological effect by modulating a signalling pathway. Typically, modulation of a signalling pathway will alter the response of a cell to a particular stimulus. For example, the effect of hormones may be modulated by targeting the kinases involved in signal transduction from the hormone receptor to the biological effectors, which are typically regulators of gene expression.

PKB is required to be phosphorylated both on residues Thr308 (in the activation loop) and Ser473 (in the C-terminal regulatory domain) for full activation. Thus, by modulating PKB Ser473 kinase's ability to phosphorylate PKB, it is possible to modulate the effects of PKB in general, such as in cell proliferation and insulin signalling. Similarly, by modulating PKB Ser 473 kinase's ability to phosphorylate its other in vivo substrates, their effects will similarly be modulated.

Accordingly, there is provided a method of modulating PKB Ser473 kinase activity in a cell comprising modulating the interaction of PKB Ser473 kinase with other proteins, such as PKB. Preferably, the method comprises bringing the cell into contact with an activator or an inhibitor of PKB Ser473 kinase activity. Activators and Inhibitors, which include PKB Ser473 kinase mimics, are referred to collectively as modulators. Inhibitors may interact with PKB Ser473 kinase to inhibit phosphorylation of Ser473 on PKB (or equivalent). Other modulators, referred to as activators, may increase PKB Ser473 kinase activity and may therefore increase phosphorylation of PKB on Ser 473 (or equivalent) and as a result may increase specific signalling (e.g., PKB signaling) in general.

In another aspect, the invention provides a method of screening for a potential modulator of PKB Ser 473 kinase activity comprising the steps of (a) incubating a purified PKB Ser 473 kinase protein as hereinabove described with a compound; (b) determining PKB Ser 473 kinase activity; and (c) detecting an alteration in the PKB Ser 473 kinase activity in the presence of the compound relative to when said compound is absent, said alteration being indicative of a potential modulator of PKB Ser 473 kinase activity. A decrease in the PKB Ser 473 kinase activity correlates with the presence of a PKB Ser 473 kinase inhibitor, useful as an anti-proliferative or anti-tumour compound, whereas an increase in the PKB Ser 473 kinase activity correlates with the presence of a PKB Ser 473 activator, useful in the treatment of any one or more of a disease or condition requiring enhanced PKB Ser 473 activity, including without limitation diabetes, neurodegenerative conditions, or erectile dysfunction.

The invention also provides a method of screening for compounds that are potential modulators of tumour cell growth, in particular inhibitors of tumour cell growth. Further provided by the present invention are modulators of PKB Ser 473 kinase activity.

Modulators of PKB Ser 473 kinase activity can be activators or inhibitors. Activators of PKB Ser 473 kinase activity are useful in the treatment of any one or more of a disease or condition including without limitation diabetes, neurodegenerative conditions, or erectile dysfunction, or of any disease or condition ameliorated by the induction of cell growth. Inhibitors of PKB Ser 473 kinase activity are useful as antiproliferative or anti-tumour agents. PKB Ser 473 kinase modulators may be formulated according to conventional methodology, depending on the exact nature of the modulator, and will typically comprise the modulator or a precursor thereof in association with a biologically acceptable carrier.

In one aspect of the present invention, the compounds identified by the screening method can be used as a pharmaceutical. In another aspect, the compound identified by the screening method can be used for the manufacture of a medicament for the treatment or prophylactic treatment of a disease or condition associated with cell growth. The compound identified by the screening method can further be used in the treatment of a condition associated with cell growth, especially for inhibiting cancer cell growth. A method for inhibiting cancer cell growth comprises contacting a cancerous cell with a PKB Ser 473 kinase inhibitor.

In another aspect of the present invention, the compounds identified by the screening method are used for treating a disease associated with an anomaly in cell growth comprising administering to a subject a pharmaceutically effective amount of a PKB Ser 473 kinase modulator. In an alternative embodiment, compounds are provided for treating a disease associated with an anomaly in insulin regulation.

Delivery of the modulator to the affected cells and tissues can be accomplished using appropriate packaging or administration systems. For example, the modulator may be formulated for therapeutic use with agents acceptable for pharmaceutical administration of proteinaceous agents and delivered to the subject by acceptable routes, such as via liposomes. Alternatively, small molecule analogs may be used and administered to act as PKB Ser473 kinase inhibitors or activators and in this manner produce a desired physiological effect.

The screening system is preferably used to screen for compounds that are modulators of PKB Ser473 kinase function, particularly where that function is related to PKB activity. The system can be used to screen small molecule libraries, peptide libraries, phage display libraries, or natural product libraries.

In order to increase the understanding of PKB Ser473 kinase activity and potentially improve PKB Ser473 kinase modulators, isolated PKB Ser473 kinase can be used to establish secondary and tertiary structure of the whole protein or at least of the areas responsible for the enzymatic activity and regulation. Conventional methods for the identification of the 3-dimensional structure are, for example, X-ray studies or NMR studies. The data obtained with these or comparable methods may be used directly or indirectly for the identification or improvement of modulators of PKB Ser473 kinase. A commonly used method in this respect is, for example, computer aided drug design or molecular modelling. A further embodiment of the invention concerns the modulator identified with the polypeptide of the invention, or with the aid of the 3-dimensional structure derived there from, for use in a method of treatment.

Kits useful for screening such compounds may also be prepared in accordance with the invention, and will comprise essentially PKB Ser473 kinase or a fragment thereof useful for screening, and instructions. Typically the PKB Ser473 kinase polypeptide will be provided together with means for determining the compound-induced modulation in the activity of the PKB Ser 473 kinase. PKB Ser473 kinase for use in kits according to the invention may be provided in the form of a protein, for example in solution, suspension or lyophilised.

In a still further embodiment, the invention provides a compound that interacts directly or indirectly with PKB Ser473 kinase or a fragment thereof, preferably a compound that modulates PKB Ser473 kinase activity. Such a compound may be inorganic or organic, for example an antibiotic or antibody, and is preferably a proteinaceous compound involved in intracellular signalling.

Compounds according to the invention may be identified by screening using the techniques described hereinbefore, and prepared by extraction from natural sources according to established procedures, or by synthesis, especially in the case of low molecular weight chemical compounds. Proteinaceous compounds may be prepared by expression in recombinant expression systems, for example a baculovirus system, or in a bacterial system. Proteinaceous compounds are mainly useful for research into the function of signalling pathways, although they may have a therapeutic application.

Low molecular weight compounds, on the other hand, are preferably produced by chemical synthesis according to established procedures. They are primarily indicated as therapeutic agents. Low molecular weight compounds and organic compounds in general may be useful as antiproliferative agents, for use in the treatment of a condition associated with cell growth, or for treating diabetes.

Administration of pharmaceutical compositions of the invention may be accomplished orally or parenterally. Methods of parenteral delivery include topical, intra-arterial (e.g. directly to the tumour), intramuscular, subcutaneous, intramedullary, intrathecal, intraventricular, intravenous, intraperitoneal, or intranasal administration. In addition to the active ingredients, these pharmaceutical compositions can contain suitable pharmaceutically acceptable carriers comprising excipients and other compounds that facilitate processing of the active compounds into preparations which can be used pharmaceutically. Further details on techniques for formulation and administration can be found in the latest edition of Remington's Pharmaceutical Sciences (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, etc, suitable for ingestion by the patient.

Pharmaceutical preparations for oral use can be obtained through combination of active compounds with solid excipient, optionally grinding a resulting mixture, and processing the mixture of granules, after adding suitable additional compounds, if desired, to obtain tablets or dragee cores. Suitable excipients are carbohydrate or protein fillers include, but are not limited to sugars, including lactose, sucrose, mannitol, or sorbitol; starch from corn, wheat, rice, potato, or other plants;

cellulose such as methyl cellulose, hydroxypropylmethylcellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores can be provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterise the quantity of active compound (i.e. dosage).

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds can be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension can also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention can be manufactured in substantial accordance with standard manufacturing procedures known in the art (e.g. by means of conventional mixing, dissolving, granulating, dragee-making, levigating, emulsifying, encapsulating, entrapping or lyophilising processes).

The invention is further described below, for the purpose of illustration only, in the following examples:

EXAMPLES

Expression Constructs, Transfection and Treatment of Cells

Expression constructs for HA-tagged PKB have been previously described (see Hill and Hemmings, 2002). Integrin-linked kinase was cloned from a human placenta cDNA library by polymerase chain reaction based on the published sequence (NIDg2648173/U40282, Hannigan et al., 1996, Nature 379: 91-96) and subcloned into pCMV5 vector. Culture and transfection of HEK 293 cells using a modified calcium phosphate method have been previously described (Andjelkovic, et al., 1999, Mol Cell Biol 19: 5061-5072). For analytical experiments, cells were starved overnight prior to treatment. Preparation and cell treatment with pervanadate was performed as previously described and total cell lysates were collected in NP-40 lysis buffer (Andjelkovic et al., 1996, Proc Natl Acad Sci USA 93: 5699-5704; Andjelkovic, et al., 1999, Mol Cell Biol 19: 5061-5072).

Example 1

Subcellular Localization of PKBSer473 Kinase

In order to characterize and purify the PKB Ser473 kinase, we reasoned that the kinase might be constitutively active at the plasma membrane (PM). To this end, we developed a subcellular fractionation protocol to generate fractions enriched in the PM. To determine the efficacy of the procedure, the fractionation behavior of products of two PKB constructs was examined: hemagglutinin (HA) tagged PKBα (HA-PKBα) and HA-PKBα containing a myristoylation/palmitylation signal (m/p-HA-PKBα).

HEK 293 cells transiently transfected with the PKB constructs were serum starved, stimulated or not with 0.1 mM pervanadate for 10 min at 37° C., and subcellular fractions were generated. Briefly, HEK 293 cells were washed once in ice-cold phosphate-buffered saline, and scraped in ice-cold fractionation buffer containing 20 mM HEPES-NaOH, pH 7.4, 250 mM sucrose, phosphatase inhibitors (10 mM sodium fluoride, 1 mM sodium pyrophosphate, 0.1 mM sodium orthovanadate, 2 µM microcystin LR [Alexis]), and protease inhibitors (1 mM PMSF and 1 mM benzamidine). After homogenization either by 10 passes through a 26-gauge needle, or by using a Kinematica homogenizer (10 strokes on speed 2 followed by 30 strokes on speed 10), subcellular fractions were prepared as previously described (Hill and Hemmings, 2002, Methods Enzymol 345: 448-463). The plasma membrane pellets were resuspended in 50 mM Tris-HCl (pH7.4) containing protease and phosphatase inhibitors as described above. Protein concentration of the subcellular fractions was determined by the Bradford method (Bio-Rad), using bovine serum albumin as standard. Fractions can be snap frozen in liquid nitrogen and stored at −80° C. for further use.

The presence of PKB in each fraction was determined by immunoblotting with an anti-HA antibody (12CA5). In addition, the phosphorylation status of PKB in each of the fractions was assessed by immunoblotting with phospho-specific PKB antibodies after immunoprecipitation with the HA antibody. Briefly, following SDS-PAGE, proteins were transferred onto Immobilon-P membranes (Millipore). Non-specific signals were blocked by incubating the membrane in TBST buffer (50 mM Tris-HCl, pH 7.4, 150 mM NaCl, 0.1% Tween-20) containing 5% skim milk for 1 hour at room temperature. Incubation with antibodies was performed in TBST for phospho-specific antibodies, TBST containing 1% skim milk for polyclonal antibodies and TBST containing 5% skim milk for monoclonal antibodies, at 4° C. overnight. Antibodies specific for PKB phosphorylated on Thr308 are commercially available (Cell Signalling Technologies). Antibodies specific for PKB phosphorylated on Ser473 was produced and purified as previously described (Hill and Hemmings, 2002, Methods Enzymol 345: 448-463). Pan-PKB antibody has been previously described (Jones et al., 1991, Proc Natl Acad Sci USA 88: 4171-4175).

Wild type PKBα was mostly present in the cytosolic fraction of starved cells. A portion of PKBα translocated to the PM fraction upon pervanadate stimulation, where the majority of phosphorylated PKBα was detected. Membrane-targeted m/p-HA-PKBα was found in both the PM fraction and the crude nuclear fraction, and no translocation was observed following stimulation. As previously reported (Andjelkovic et al., 1997, J Biol Chem 272: 31515-31524), m/p-HA-PKBα was phosphorylated on both Thr308 and Ser473 in both stimulated and unstimulated cells. In agreement that the Ser473 kinase is constitutively active at the PM, m/p-HA-PKBα was highly phosphorylated in the PM fraction on both Thr308 and Ser473 in an agonist-independent manner.

Once the fractionation procedure was established based on localization of known proteins, the subcellular localization of PKB Ser473 kinase was determined. PKB Ser473 kinase activity was found to be enriched in the plasma membrane fraction where it is constitutively active but sensitive to PI 3-kinase inhibition. In brief, Ser473 kinase activity in subcellular fractions generated from wild type HEK 293 cells was measured in vitro using two peptides as substrates: RRPHFPQFSYSASSTA (FSY peptide; SEQ ID NO:1), corresponding to the last 16 amino acids of PKBα, and the control peptide RRPHFPQFAYSASSTA (SEQ ID NO:2), where Ser473 is changed to an alanine (FAY peptide). These two peptides were used as substrates for several reasons. By using the FSY and FAY peptides, kinase activity specific for the Ser473 site could be conveniently identified. Results with the FAY indicated the existence of non-specific kinase activity in the partially purified fractions capable of phosphorylating other Ser/Thr or Tyr residues in this sequence. In order to confirm that the kinase activity isolated was specific for Ser473 within the hydrophobic site of PKB, baculovirus PKB produced protein was also tested as substrate followed by phospho-site immunoblotting.

Assays were performed in a 50-μl reaction volume, in a buffer containing 50 mM Tris-HCl (pH7.4), 1 mM DTT, 10 MgCl$_2$, 1 μM PKI, 50 mM ATP, 0.15 μCi [γ$^{32}$P]ATP, 0.1 mg/ml substrate (FSY) or control (FAY) peptide. After incubating for 60 min at 30° C. with shaking, reactions were stopped by adding 5 μl of 100% (w/v) trichloroacetic acid. Proteins were pelleted by centrifugation at 15,000 g for 10 min at room temperature. An aliquot (35 μl) of the supernatant was spotted onto squares of P81 paper (Whatmann), and washed extensively in 1% phosphoric acid. After a final rinse in acetone, P81 papers were air-dried and analyzed by scintillation counting. In some experiments, recombinant ΔPH-PKBβ, produced in the baculovirus system using conventional methods (Yang et al., 2002) was used as substrate, and phosphorylation was detected by immunoblotting with phospho-specific antibodies, essentially as described above.

The total protein in the cytosolic fraction was usually 10 times more than that in the plasma membrane fraction. Moreover, specific enzyme activity for Ser473 phosphorylation was found to be highly enriched in the PM fraction of HEK 293 cells providing an effective means of purification for the Ser473 kinase. In contrast, PKB and PDK1 are mainly located in the cytosolic fraction of unstimulated cells (Park et al., 2001, J Biol Chem 276: 37459-37471). As the Ser473 kinase is highly enriched in the plasma membrane fraction, it is unlikely that either PKB or PDK1 is the Ser473 kinase in vivo. Furthermore, PKB does not autophosphorylate on Ser473, under conditions where the partially purified Ser473 kinase preparation could phosphorylate various PKB isoforms, including a kinase inactive mutant of PKBα.

Next, it was examined if membrane-associated Ser473 kinase activity was dependent on PI3-kinase signalling. Serum-starved HEK293 cells were treated with 0.1 microM insulin, the insulin mimetic pervanadate (0.1 mM, 10 mins.), the PI 3-kinase inhibitor LY294002 (50 microM, 30 mins.), or left untreated. PM fractions were assayed for Ser473 kinase activity, and also analyzed by immunoblotting for phospho-PKB and total PKB. In agreement with previous results (Alessi et al., 1996, EMBO J. 15: 6541-6551; Andjelkovic et al., 1996, Proc Natl Acad Sci USA 93: 5699-5704), insulin and pervanadate induced PKB phosphorylation on both Thr308 and Ser473, with pervanadate being a more potent activator of PKB phosphorylation than insulin. However, neither stimuli increased Ser473 kinase activity above basal levels. Treatment of serum-starved cells with the PI3-kinase inhibitor LY294002 attenuated the activity of the Ser473 kinase. An increase in Ser473 kinase activity In the cytosolic fraction following LY294002 treatment was not observed, suggesting that the Ser 473 kinase is inactive when not bound to the membrane or to its cofactors localized at the membrane.

The nature of the association of the Ser473 kinase with the plasma membrane was therefore further characterized. Plasma membrane fractions prepared from HEK 293 cells were thawed and pelleted at 100,000 g for 30 min. After removal of the supernatant, the membrane pellets were resuspended in 50 mM Tris-HCl (pH7.4) containing either 1% Triton X-100 or 0.5 M NaCl. Following a 30-min incubation at 4° C., insoluble proteins were pelleted by centrifugation at 100,000 g for 30 min.

Extraction of the PM fraction with a high ionic strength buffer (0.5 M) released the Ser473 kinase from the lipid bilayer, with activity detected mainly in the supernatant. This suggests that the Ser473 kinase is not an integral membrane protein, but is likely associated with the plasma membrane via protein/protein or electrostatic interactions. Interestingly, when the PM fraction was treated with 1% Triton X-100, Ser473 kinase activity was highly enriched in the insoluble fraction. Insolubility in 1% Triton X-100 at 4° C. is characteristic of cholesterol- and glycosphingolipid-rich microdomains of the plasma membranes, termed lipid rafts (Simons and Toomre, 2000, Nature Rev. 1: 31-39; Galbiati et al., 2001, Cell 106: 403-411).

To test whether PKB Ser473 kinase is localized within lipid rafts, two marker proteins were used to confirm the efficacy of the detergent extraction: flotillin, an integral membrane protein associated with lipid rafts (Bickel et al., 1997, J Biol Chem 272: 13793-13802), and Na$^+$/K$^+$ ATPase, a non-raft integral plasma membrane protein. Antibodies against flotillin are commercially available from Transduction Labs, whereas antibodies against Na$^+$/K$^+$ ATPase are prepared by standard procedures. Like the Ser473 kinase activity, flotillin was detected in the Triton X-100-insoluble (pellet) fraction of the plasma membrane, while the Na$^+$/K$^+$ ATPase was solubilized In the presence of 1% Triton X-100. As expected for integral membrane proteins, both Na$^+$/K$^+$ ATPase and flotillin remained in the pellet fraction after extraction with 0.5 M NaCl.

Since ILK is a candidate Ser473 kinase reported to be located at the plasma membrane, also these fractions were immunoblotted with an antibody to ILK (commercially available, e.g., from UBI). ILK was detected in both the supernatant and the pellet fractions from both detergent and salt extractions, but appears to be slightly enriched in fractions with high PKB Ser473 kinase activity. These data together suggest that the PKB Ser473 kinase is associated with lipids rafts in cells.

Example 2

Sucrose Flotation Gradient Analysis

In addition to Insolubility in Triton X-100 at 4° C., lipid rafts are also characterized by their buoyancy in sucrose density gradients (Simons and Toomre, 2000, Nature Rev. 1: 31-39). To further verify the lipid raft association of the PKB Ser473 kinase, the Triton X-100-insoluble fraction of the plasma membrane was subjected to a 5%-35% step sucrose gradient, and then assayed for PKB Ser473 kinase activity. Briefly, Triton X-100 Insoluble proteins were resuspended in 1.5 ml of Buffer A (50 mM Tris-HCl, pH 7.4, 150 mM NaCl) containing 40% (w/v) sucrose, and placed in a 13.2-ml ultracentrifuge tube. A step gradient was formed above the load by successively layering 1.5 ml of buffer containing 35%, 30%, 25%, 20%, 15%, 10% and 5% of sucrose. The remaining volume was filled up with buffer A. After centrifugation at 250,000 g (39,000 rpm in a Beckman Sw41 rotor) for 18 h, 1-ml fractions were collected from the top of the tube and assayed for kinase activity essentially as described above.

The majority of the Triton X-100-insoluble protein remained at the bottom of the gradient (loading position), with a small protein peak detected in fraction 9. In contrast, the main peak of PKB Ser473 kinase activity floated to fractions 5 and 6 of the gradient, with minor activities detected in fractions 9 and 13 (FIG. 1). Aliquots of fractions 3 to 13 were subjected to in vitro phosphorylation reactions to detect the activity of kinases within these fractions. In vitro phosphorylation of flotation gradient fractions was performed by adding 1 mM DTT, 10 mM $MgCl_2$, 1 µM PKI (final concentrations) and 0.5-1 µCi [$\gamma^{32}P$]ATP to 20 µl of each fraction, and incubating for 60 min at 30° C. with shaking. Reactions were stopped by addition of Laemmli sample buffer, heated at 95° C. for 5 min, and then analyzed by SDS-PAGE and autoradiography. Interestingly, fractions 4 to 10 showed a remarkably similar pattern of phosphorylated proteins comprising phosphoproteins of 40 kDa and 80 kDa, in addition to several phosphoproteins between 50 and 60 kDa. Despite the similarity in phosphoprotein profiles of the buoyant fractions (4 to 10), flotillin was detected only in fractions 7, 8, with some material remaining in the loading position (fraction 13). This apparent disparity may be due to heterogeneity in the lipid rafts, such that the sucrose gradient used in our experiments allowed the separation of rafts with different buoyancy, but phosphorylation on Ser473 was only detected in fractions 5 and 6. Significantly, while the PKB Ser473 kinase activity was enriched in fractions 5 and 6, ILK was detected in all fractions.

Example 3

Gel Filtration Analysis

Example 2 demonstrates that the PKB Ser473 kinase activity is enriched in a detergent-insoluble, buoyant-density fraction of the plasma membrane, and the association of this kinase with the membrane can be disrupted by high ionic strength. To further investigate the nature of this interaction, we analyzed the NaCl-extracted fraction of the plasma membrane by gel filtration analysis using a Superdex-200 column. Gel filtration was performed with a Superdex-200 HR10/30 column attached to a FPLC system (Amersham Pharmacia Biotech). Briefly, the column was equilibrated with buffer B (20 mM Tris-HCl, pH7.4, 0.5 M NaCl, 1 mM DTT and 1 mM benzamidine). The supernatant (0.5-ml) from 0.5 M NaCl treatment was loaded onto the column. Buffer B was pumped at a flow rate 0.5 ml/min, and fractions were collected every minute. Molecular weight markers for gel filtration chromatography were from Sigma and included blue dextran (2000 kDa), apoferritin (443 kDa) and beta-amylase (200 kDa).

Figure 2:
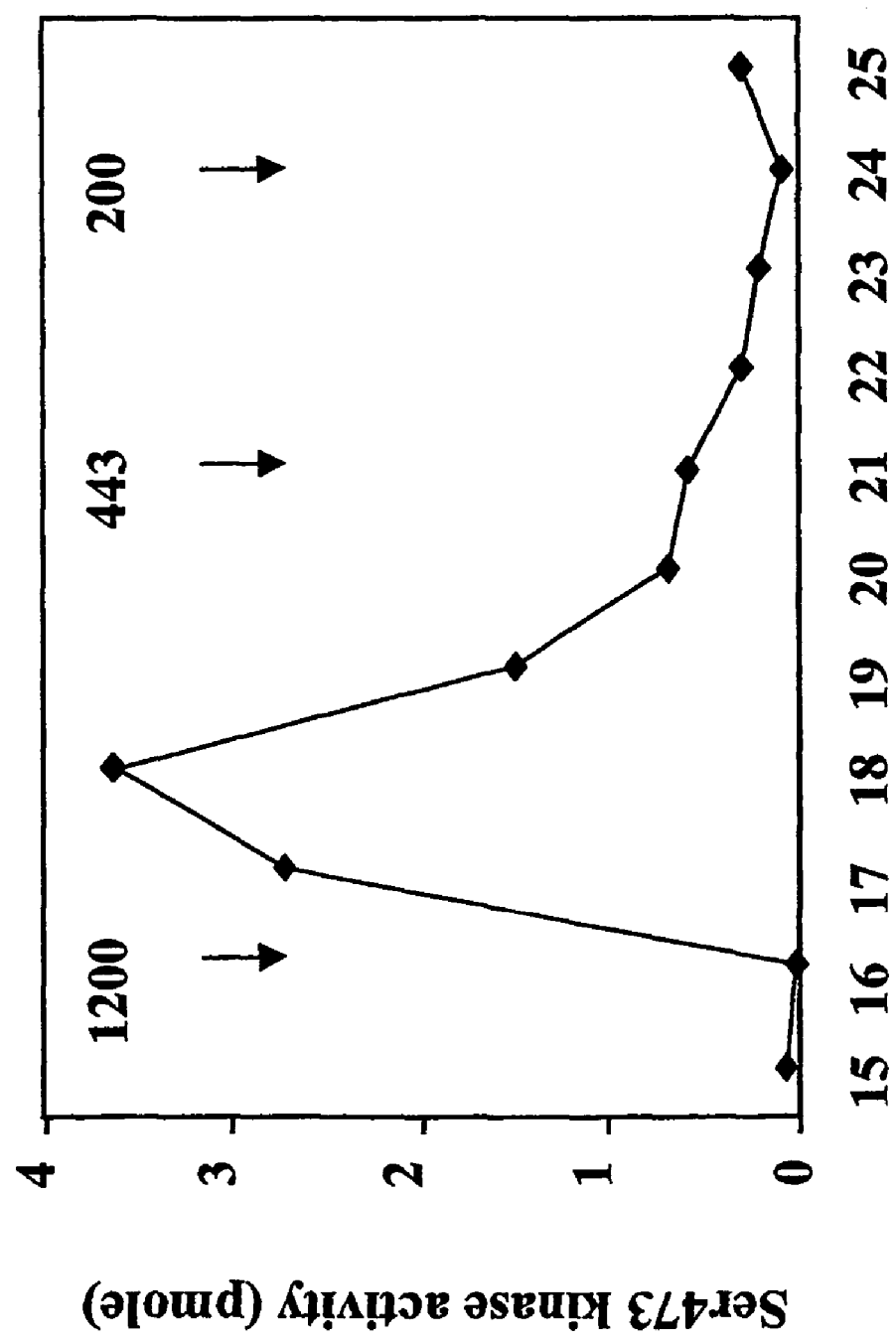
FIG. 2 is a schematic diagram of 0.5M NaCl extracted plasma membrane fraction subjected to gel filtration on a Superdex 200 column. The standards are indicated by arrows.

PKB Ser473 kinase activity of eluates was monitored essentially as described in Example 2. The major peak of kinase activity eluted at an approximate mass of ~550 kDa, suggesting that the kinase is part of a large protein complex. To verify that this kinase also phosphorylates PKB protein, recombinant ΔPH-PKBβ protein was used as a substrate to assay fractions from the Superdex-200 column. The ΔPH-PKBβ protein was not phosphorylated on Ser473 as determined by mass spectrometry and phospho-immunoblotting. Phosphorylation of ΔPH-PKBβ by Superdex 200 column fractions was monitored using phospho-Ser473-specific antibodies. As observed in the peptide kinase assay, the PKB Ser473 kinase activity eluted in fraction 17 to 20 (FIG. 2). Significantly using a highly purified crystallization grade PKB, no autophosphorylation of PKB could be seen. Phosphorylation of Ser473 of the PKBβ preparation was dependent upon the addition of the partially purified Ser473 kinase.

In vitro phosphorylation reactions of the peak activity fractions from the Superdex-200 column revealed two prominent phosphoproteins of 48 kDa and 58 kDa, which coincide with the PKB Ser473 kinase activity. ILK protein levels also closely paralleled that of the PKB Ser473 kinase activity on the gel filtration profile.

Example 4

MonoQ FPLC Column Chromatography

Ion exchange chromatography using MonoQ FPLC to further Isolate the Superdex-200 Ser-473 kinase fractions. Fractions from the Superdex 2000 column are diluted (10 times) in buffer A (20 mM Tris/HCL, pH 7.5, 1 mM DTT, 1 mM EDTA, 5% glycerol, 1 mM benzamidine, and 1 mM PMSF) and are applied to a MONO Q HR5/5 column equilibrated with buffer A. The column is washed with buffer A and developed with a 30 ml linear gradient of 0 to 0.6 M NaCl in Buffer A. Fractions of 0.5 ml eluting from the column are collected and assayed for Ser473 kinase activity as described above.

Attempts to further purify the Ser473 kinase by ion exchange chromatography resulted in a loss of activity, suggesting that the PKB Ser473 kinase is a multi-subunit enzyme, or requires accessory factors.

Example 5

Characterization of Partially Purified PKB Ser473 Kinase Activity

The ability of the partially purified PKB Ser473 kinase to phosphorylate full length PKBα, PKBβ and PKBγ, as well as kinase-inactive (K179A) and phosphorylation site mutants (T308A and S473A) of PKBα was examined. HA-tagged PKB constructs were expressed in HEK 293 cells, and HA-tagged PKB proteins were immunoprecipitated from lysates in NP-40 lysis buffer using 12CA5 antibodies (Roche Biochemicals) pre-coupled to Protein A-Sepharose. After incubating for 2 h at 4° C., beads were washed once in lysis buffer supplemented with 0.5 M NaCl, once in lysis buffer and then finally in 50 mM Tris-HCl, pH 7.4. Prior to kinase reactions, dephosphorylation with γ-phosphatase (Cell Signaling Technologies) was performed for 30 min at 30° C. according to manufacturer's instructions. Beads were washed as described previously, and then incubated in kinase reaction buffer with/without pooled Superdex-200 fractions for 60 min at 30° C. As a control, half of the immunoprecipitated PKB proteins were incubated in kinase reaction buffer without adding pooled peak activity fractions from the Superdex-200 column. After kinase reaction, beads were washed 2 times in NP-40 lysis buffer, and then heated at 95° C. in SDS-PAGE sample buffer before analysis by SDS-PAGE and immunoblotting. PKB Ser473 phosphorylation was detected by immunoblotting with a phospho-Ser473-specific antibody.

When incubated in kinase reaction buffer alone, PKB isoforms and mutants were not phosphorylated on Ser473, suggesting that PKB does not autophosphorylate on Ser473 under these conditions. When incubated with partially purified Ser473 kinase, all PKB proteins with the exception of the S473A mutant were phosphorylated on Ser473. Notably, the ATP binding site mutant K179A, and the activation loop phosphorylation site mutant T308A were not impaired in their ability to be phosphorylated on Ser473, suggesting that PKB kinase activity is not required for maximal Ser473 kinase activity.

Example 6

Staurosporine Sensitivity of Ser473 Kinase Activity

It has previously been shown that insulin-stimulated phosphorylation on Ser473 occurs via a staurosporine-insensitive kinase (Hill et al., 2001, J Biol Chem 276: 25643-25646). Thus, we were interested to determine the staurosporine sensitivity of the partially purified kinase. Peak activity fractions from the Superdex-200 column were pooled and then assayed for PKB Ser473 kinase activity using the FSY peptide essentially as described above, in the presence of varying concentrations of staurosporine (0, 0.001, 0.01, 0.1, 1, 10 and 100 microM). This assay revealed the presence of two distinct kinase activities in the partially purified fraction: one acutely sensitive to staurosporine, with inhibition observed at 1 nM, while the other is insensitive up to 100 µM staurosporine. Our previous results would suggest that only the latter activity corresponds to the PKB Ser473 kinase.

Example 7

ILK Does not Play an Active Role in the Phosphorylation of PKB on Ser473

Since ILK was detected in the sucrose gradient fractions and in the peak fractions of the gel filtration column, the role of ILK was directly assessed in plasma membrane-associated PKB Ser473 kinase activity. ILK was immunoprecipitated from NaCl-extracted plasma membrane fraction, and then both the immunoprecipitate and the supernatant were assayed for PKB Ser473 kinase activity. Briefly, NaCl-extracted plasma membrane fraction (in 50 mM Tris-HCl, pH 7.4, 0.5 M NaCl) was precleared using Sepharose 4B for 1 h at 4° C., and then immunoprecipitated using ILK antibodies (UBI) pre-coupled to Protein A-Sepharose for 2 h at 4° C. The supernatant was collected for assays. The immunoprecipitate was washed 2 times in 50 mM Tris-HCl, pH 7.4, 0.5 M NaCl, once in 50 mM Tris-HCl, pH 7.4 prior to kinase assays carried out essentially as described above.

The PKB Ser473 kinase activity was detected in the supernatant after immunoprecipitation, regardless of whether ILK or normal rabbit serum was used for immunoprecipitation. No significant Ser473 kinase activity was detected in the ILK immunoprecipitate, where the presence of ILK was confirmed by immunoblotting. Furthermore, no significant phosphorylation of PKB on Ser473 upon overexpression of ILK in HEK 293 cells was observed, both under basal conditions, and in addition to insulin stimulation. These data suggest that ILK cannot serve as the PKB Ser473 kinase.

Several lines of evidence distinguish the PKB Ser473 kinase activity isolated by the present invention from ILK. Insulin activates ILK in a PI 3-kinase-dependent manner (Delcommenne et al., 1998, Proc Natl Acad Sci USA 95: 11211-11216), in contrast to the constitutively active Ser473 kinase activity described hereinabove, which was not further activated by growth factors. While both Ser473 kinase activity and ILK can be found in the Triton X-100-insoluble fraction of the plasma membrane, they showed distinct behavior on sucrose flotation gradient. Furthermore, Ser473 kinase activity was detected in the supernatant, but not in ILK immunoprecipitates from the membrane fraction. Finally, no effect of ILK overexpression on PKB Ser473 phosphorylation could be detected. Furthermore, it was recently found that Ser473 phosphorylation of *Drosophila* PKB In ILK knockout embryos is comparable to wild type embryos, providing further evidence that ILK is not the PKB Ser473 kinase.

In summary, the present inventors have investigated the regulation of PKB by phosphorylation and have therefore purified PKB Ser473 kinase from a cell culture system. The inventors found that the PKB Ser473 kinase was enriched in raft-like fractions of the plasma membrane of human embryonic kidney (HEK) 293 cells, and its constitutive activity was dependent on PI 3-kinase. Association of the PKB Ser473 kinase with the plasma membrane was found to occur via protein-protein interactions, as it could be released from membranes by high salt extraction. ILK was found to co-fractionate with the Ser473 kinase activity. However, no significant PKB Ser473 kinase activity could be detected in the ILK immunoprecipitates from salt-extracted plasma membrane fraction. The present inventors show that ILK is not the PKB Ser473 kinase per se. Two candidate phosphoproteins of 48 kDa and 58 kDa respectively were identified, which co-fractionate with the PKB Ser473 kinase activity both on sucrose density gradient and by gel-filtration. It was demonstrated that a PKB Ser473 kinase exists at the plasma membrane of cells.

What is claimed is:

1. A purified PKB Ser 473 kinase complex, which has PKB Ser 473 kinase activity and an apparent molecular weight of 450-650 kDa when fractionated by gel filtration chromatography, wherein the purified PKB Ser 473 kinase complex has been isolated from a cell-free extract that has measurable PKB Ser 473 kinase activity in 0.2 µg of protein when detected in a kinase assay in which a PKB peptide substrate is phosphorylated with $^{32}$P labeled phosphate, wherein the purified PKB Ser 473 kinase complex elutes with the apparent molecular weight of 450-650 kDa when fractionated by the gel filtration chromatography and the measurable PKB Ser 473 kinase activity in the cell-free extract is at least 2000 times greater than a PKB Ser 473 kinase activity in a crude cell extract, wherein the kinase activities are measured using the kinase assay.

2. A purified cell extract that has measurable PKB Ser 473 kinase activity in 0.2 µg of protein when detected in a kinase assay in which a PKB peptide substrate is phosphorylated with $^{32}$P labeled phosphate, wherein a kinase complex elutes with an apparent molecular weight of 450-650 kDa when fractionated by gel filtration chromatography and the measurable PKB Ser 473 kinase activity in the purified cell extract is at least 2000 times greater than a PKB Ser 473 kinase activity in a crude cell extract, wherein the kinase activities are measured using the kinase assay.

3. The purified cell extract of claim 2, wherein the kinase complex elutes with an apparent molecular weight of 550 kDa when fractionated by gel filtration chromatography.

4. A method of screening for a potential modulator of PKB Ser 473 kinase activity comprising the steps of:
   (i) incubating the purified PKB Ser 473 kinase protein complex of claim 1 with a compound;
   (ii) determining PKB Ser 473 kinase activity; and
   (iii) detecting an alteration in the PKB Ser 473 kinase activity in the presence of the compound relative to when the compound is absent, the alteration being indicative of a potential modulator of PKB Ser 473 kinase activity.

5. The method according to claim 4, wherein the alteration in the PKB Ser 473 kinase activity is a decrease in PKB Ser 473 kinase activity, the decrease being indicative of a potential inhibitor of PKB Ser 473 kinase.

6. The method according to claim 4 wherein the alteration in the PKB Ser 473 kinase activity is an increase in the PKB Ser 473 kinase activity, the increase being indicative of a potential activator of PKB Ser 473 kinase.

* * * * *

SEQUENCE LISTING

<160> NUMBER OF SEQ ID NOS: 2

<210> SEQ ID NO 1
<211> LENGTH: 16
<212> TYPE: PRT
<213> ORGANISM: homo sapiens

<400> SEQUENCE: 1

Arg Arg Pro His Phe Pro Gln Phe Ser Tyr Ser Ala Ser Ser Thr Ala

```
                                          -continued 1               5               10              15

<210> SEQ ID NO 2
<211> LENGTH: 16
<212> TYPE: PRT
<213> ORGANISM: artificial sequence
<220> FEATURE:
<223> OTHER INFORMATION: Designed non-phosphorylatable Ala "473" peptide
      based on phosphorylatable substrate

<400> SEQUENCE: 2

Arg Arg Pro His Phe Pro Gln Phe Ala Tyr Ser Ala Ser Ser Thr Ala
1               5                   10                  15
```